(12) United States Patent
Fitch et al.

(10) Patent No.: US 9,982,838 B2
(45) Date of Patent: May 29, 2018

(54) CONDITION MONITORING POD

(71) Applicant: Luneta, LLC, Tulsa, OK (US)

(72) Inventors: James Chester Fitch, Tulsa, OK (US); Thomas Chester Fitch, Tulsa, OK (US); Michael Anthony Ramsey, Tulsa, OK (US)

(73) Assignee: Luneta, LLC, Tulsa, OK (US)

( * ) Notice: Subject to any disclaimer, the term of this patent is extended or adjusted under 35 U.S.C. 154(b) by 757 days.

(21) Appl. No.: 14/242,395

(22) Filed: Apr. 1, 2014

(65) Prior Publication Data
US 2014/0311240 A1 Oct. 23, 2014

Related U.S. Application Data

(60) Provisional application No. 61/807,158, filed on Apr. 1, 2013.

(51) Int. Cl.
| | |
|---|---|
| *F16N 19/00* | (2006.01) |
| *F16N 29/00* | (2006.01) |
| *F01M 11/04* | (2006.01) |
| *F01M 11/10* | (2006.01) |
| *F01M 11/12* | (2006.01) |

(52) U.S. Cl.
CPC ....... F16N 19/003 (2013.01); F01M 11/0408 (2013.01); F16N 19/00 (2013.01); F16N 29/00 (2013.01); *F01M 11/0458* (2013.01); *F01M 11/12* (2013.01); *F01M 2011/0425* (2013.01);
(Continued)

(58) Field of Classification Search
CPC ............... G01N 33/2888; G01N 33/30; F01M 2011/14; F16N 19/00; F16N 29/00
See application file for complete search history.

(56) References Cited

U.S. PATENT DOCUMENTS 2,320,048 A * 5/1943 Parson ............... F01M 11/0458
134/113
3,923,657 A 12/1975 Roser
(Continued)

FOREIGN PATENT DOCUMENTS

JP 07286943 A * 10/1995

OTHER PUBLICATIONS

International Search Report and Written Opinion for Application PCT/US2014/032542 dated Dec. 16, 2014.
(Continued)

*Primary Examiner* — Paul West
(74) *Attorney, Agent, or Firm* — Dunlap Codding, P.C.

(57) ABSTRACT

Apparatuses are disclosed including an apparatus for machine fluid monitoring or sampling comprising a transparent sight glass attachable to a machine such that machine fluid is transferable to the sight glass. The sight glass may have one or more ports, an open first end, a closed second end, and a cavity for the machine fluid. A grommet may be positioned in a first port of the sight glass and may have a sealable access pathway through the grommet to the cavity within the sight glass through which a probe may be extended. A magnetic plug may be positioned in the second port of the sight glass extending into the cavity within the sight glass such that the magnetic plug is positionable for contact with the machine fluid. A sample port assembly may be connected to the sight glass whereby samples of the machine fluid are accessible.

17 Claims, 6 Drawing Sheets

(52) U.S. Cl.
CPC .. *F01M 2011/0491* (2013.01); *F01M 2011/14* (2013.01)

(56) References Cited

U.S. PATENT DOCUMENTS

| | | | | |
|---|---|---|---|---|
| 4,065,348 | A * | 12/1977 | Zimmerman | ........ D21C 9/1052 162/238 |
| 4,468,613 | A | 8/1984 | Slough et al. | |
| 4,557,216 | A | 12/1985 | Demyon | |
| 4,615,413 | A | 10/1986 | Stevenson | |
| 4,827,770 | A | 5/1989 | Schwartz et al. | |
| 4,888,990 | A | 12/1989 | Bryan et al. | |
| 4,993,460 | A | 2/1991 | Robinson et al. | |
| 5,243,929 | A | 9/1993 | Brown et al. | |
| 5,611,241 | A * | 3/1997 | Henry | ............ G01F 23/02 116/276 |
| 5,628,231 | A | 5/1997 | Sheridan | |
| 6,082,972 | A | 6/2000 | Moore, Jr. et al. | |
| 6,380,746 | B1 * | 4/2002 | Polczynski | ........ G01N 33/2888 324/439 |
| 6,558,541 | B1 * | 5/2003 | Morrison | ............ B03C 1/286 184/6.25 |
| 7,788,973 | B2 * | 9/2010 | Quill | ............ F04B 51/00 73/290 V |
| 8,316,653 | B2 | 11/2012 | Appler et al. | |
| 2010/0107496 | A1 | 5/2010 | Faria | |
| 2010/0269584 | A1 * | 10/2010 | Horst | ............ G01F 23/02 73/293 |
| 2014/0238156 | A1 * | 8/2014 | Aljohani | ............ G01N 1/10 73/864.63 |
| 2014/0311240 | A1 | 10/2014 | Fitch et al. | |

OTHER PUBLICATIONS

Kipp—Dome oil level sight glasses; http://www.kipp.com/c1/en/Products/Operating-parts-standard-elements/Level-indicators-Screw-plugs/pid.1097.1226/agid.13228.1842/ecm.ag/Dome-oil-le, Nov. 21, 2014.
Trico Corp Viewport 3D Plastic Lens, http://www.tricocorp.com/product/viewports-3d-plastic-lens, Nov. 21, 2014.
3D Bullseye, 3D Bullseye Oil Sight Glass-3D Oil Level Glass Esco Products, http://www.escopro.com/oil-sight-glass/3d-bulls-eye.html, Nov. 20, 2014.
Horizontal Oil Sight Glass, Horizontal Oil Sight Glass-Horizontal Oil Sight Glass-Oil Sight Glass Product Line, Esco Products, http://www.escopro.com/oil-sight-glass/horizontal-esco-oil-signt-glass/horizontl-oil-sight-glass.html, Nov. 20, 2014.
Sight Glass W/O-Ring, Sight Glass W/O-Ring [33-RG-001]—$6.99: Midwest Bus Parts, We do More than Bus Parts, http://www.midwestbusparts.com/index.php?main_page=product_infor&cPath-25_715&products_id=32998&zenid-fgunfjhrmlohvmiec8d9oe71i2, Nov. 21, 2014.
Sump Bottles, BS&W Bowl-Trico Corp., http://www.tricocorp.com/product/sump-bottles/, Nov. 20, 2014.

* cited by examiner

CONDITION MONITORING POD

INCORPORATION BY REFERENCE

The present patent application incorporates by reference the entire provisional patent application identified by U.S. Ser. No. 61/807,158, filed on Apr. 1, 2013.

FIELD OF THE DISCLOSURE

The disclosure generally relates to methods and apparatuses for monitoring machine fluids, such as lubricants in machinery. More particularly, but not by way of limitation, the disclosure relates to apparatuses adapted for easy access, testing, and monitoring of machine fluids in machinery, such as, but not limited to, oil within manufacturing equipment.

BACKGROUND

Most machines used in manufacturing and other industries require machine fluids for lubrication and function of machine components. Exemplary machine fluids include lubricants and oils which may be based upon hydrocarbon, synthetic and/or petroleum based products. Other types of machine fluids include hydraulic fluids. The machine fluids typically must be maintained within a preferred range of composition and cleanliness for efficient performance of the machine. For example, when oil is used as a machine fluid, the unwanted addition of water or debris may cause the machine to loose efficiency or sustain damage.

In the past, machine fluids are monitored through the collection and analysis of samples of the machine fluid. However, some current sampling and monitoring processes are inefficient, time consuming, and costly. For example, sampling may be taken from the bottom of the sump of machines (e.g., from drain ports), which can mix the lubricant with sediment making effective oil monitoring difficult. Or, sampling may require that the machine be stopped or even drained of lubricant, causing a loss of production of the machine. The best sample location and device enables the lubricant to be sampled from moving (representative) fluid without temporary loss of production. Therefore, an apparatus is needed to more efficiently monitor (through onsite inspection techniques) and sample machine liquids from a single location.

SUMMARY

Apparatuses are disclosed that facilitate efficient monitoring and/or sampling of a machine fluid within a machine. The problem of inefficient machine fluid monitoring and sampling is addressed through a condition monitoring pod optionally having a sight glass at least partially constructed of transparent material and having one or more ports configured to provide a variety of monitoring and/or analysis functions.

BRIEF DESCRIPTION OF THE DRAWINGS

The accompanying drawings, which are incorporated in and constitute a part of this specification, illustrate one or more implementations described herein and, together with the description, explain these implementations. The drawings are not intended to be drawn to scale, and certain features and certain views of the figures may be shown exaggerated, to scale or in schematic in the interest of clarity and conciseness. Not every component may be labeled in every drawing. Like reference numerals in the figures may represent and refer to the same or similar element or function. In the drawings.

DETAILED DESCRIPTION

Figure 1:
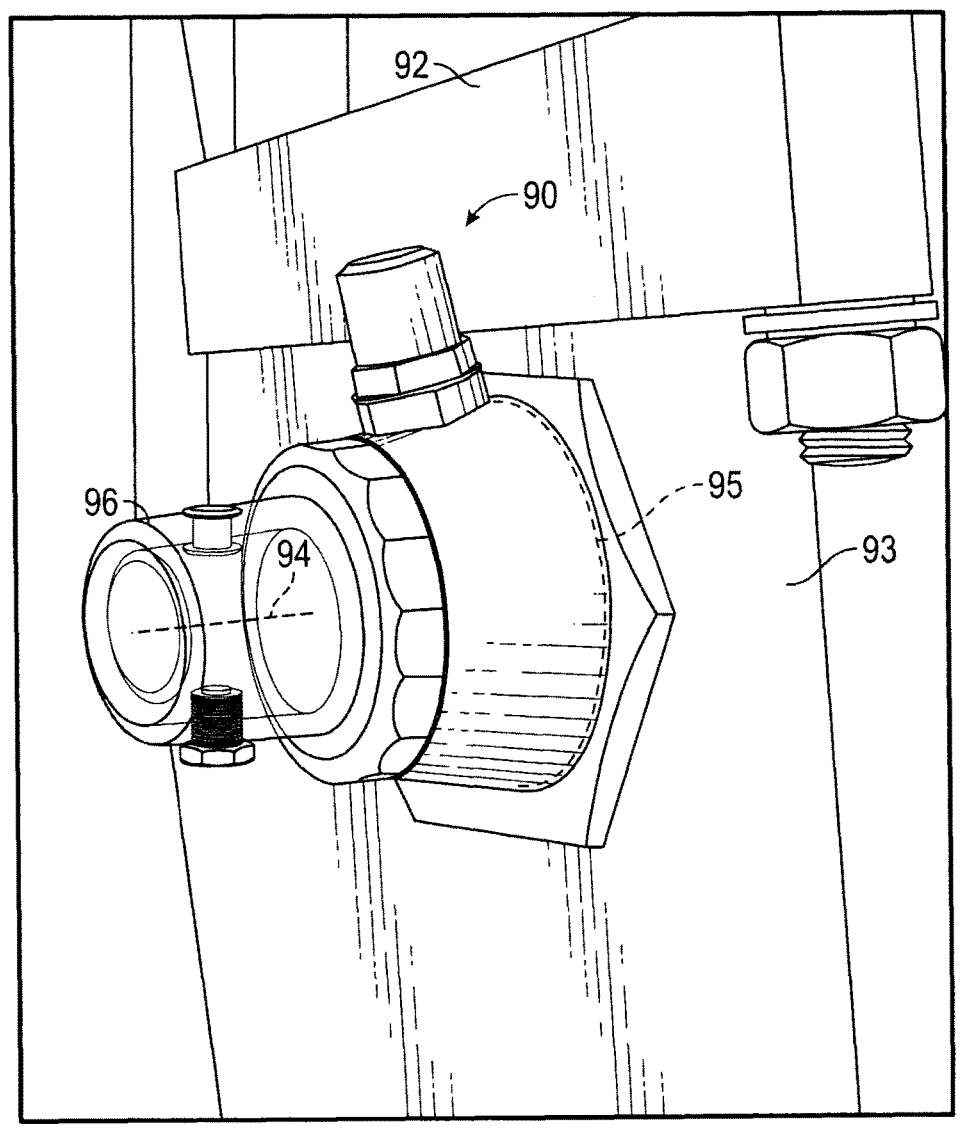
FIG. 1 is a perspective view of an exemplary condition monitoring pod (CMP) assembly mounted to a machine in accordance with the present disclosure such that a machine fluid within the machine enters into the condition monitoring pod and is visible to a person monitoring the condition of the machine fluid.

The following detailed description refers to the accompanying drawings. The same reference numbers in different drawings may identify the same or similar elements.

The mechanisms proposed in this disclosure circumvent the problems described above. The present disclosure describes a condition monitoring pod assembly for monitoring and sampling a machine fluid using a sight glass at least partially constructed of a material that is transparent to light within a visible region and having one or more ports for monitoring functions in addition to visible inspection of the machine fluid. The exemplary embodiment of the condition monitoring pod assembly comprises a sight glass at least partially constructed of one or more materials that is transparent to light in a visible region, the sight glass having an open first end, a closed second end, an inside surface and an outside surface extending from the open first end to the closed second end and forming a cavity within the sight glass, the sight glass further having a first port and a second port, the first port and the second port extending from the cavity through the inside surface and the outside surface, wherein the open first end of the sight glass is configured to be attachable to a machine such that machine fluid is transferable from the machine to the cavity of the sight glass. The assembly may further comprise a probe extending through the first port and into the sight glass cavity and a grommet positioned in the first port of the sight glass, the grommet having a sealable access pathway through the grommet to the cavity within the sight glass, the probe extending through the access pathway into the cavity within the sight glass. The probe may be designed to interact with predetermined constituents of the machine fluid for aiding the user in detecting the presence or absence of the predetermined constituents in the machine fluid. For example, the probe may be constructed of a material, such as steel, which rusts in the presence of water. If water is within the machine fluid, the probe will rust thereby providing a visual indication to the user viewing the probe through the sight glass that water is within (i.e., a constituent of) the machine fluid and the rust inhibitor additive is no longer effective.

In one embodiment, the assembly further comprises a magnetic plug positioned in the second port of the sight glass and extending into the cavity within the sight glass such that the magnetic plug is positionable for contact with the machine fluid. The magnetic plug may include a magnet which produces a magnetic field to attract and retain particles within the machine fluid that are composed of a ferromagnetic material, such as iron. The particles may be formed by the frictional surfaces of gears, bearings or other components of the machine exposed to abrasion, galling, and surface fatigue. In particular, the shape and/or properties of the particles provide an indication as to operating condition of the machine that may not otherwise be visible or known to the operator without laboratory analysis of an oil sample. The magnet may be a permanent magnet or an electromagnet.

In one embodiment, the condition monitoring pod assembly further comprises a sample port assembly extending through the sight glass or adjacent to the sight glass. The sample port assembly has a first end, a second end, an inside surface and an outside surface. The inside surface and the outside surface extend from the first end to the second end. The inside surface at least partially or completely surrounds and forms a sealable access pathway whereby one or more samples of the machine fluid is accessible through the sealable access pathway. The sample port assembly may also have a valve positioned within the sealable access pathway to permit a user to open the valve and remove a sample of a machine fluid and then close the valve to seal the sealable access pathway preferably without having to stop or otherwise alter the operating condition of the machine. The sample port assembly may also have a pilot tube extending from the sealable access pathway into the active flow of the machine fluid so as to access a sample reflective of actual conditions within the machine.

DESCRIPTION

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concept. This description should be read to include one or more and the singular also includes the plural unless it is obvious that it is meant otherwise.

Further, use of the term "plurality" is meant to convey "more than one" unless expressly stated to the contrary.

Finally, as used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As discussed above, current systems for monitoring and sampling machine lubricants are inefficient, costly, and time consuming. The present disclosure addresses these deficiencies, in one embodiment, with an apparatus for monitoring and sampling machine liquids comprising a sight glass assembly having a sight glass at least partially constructed of transparent material and having one or more ports for multiple monitoring functions.

Referring now to the drawings, FIG. 1 is a perspective view of an exemplary condition monitoring pod (CMP) assembly 90 mounted to a machine 92 in accordance with the present disclosure such that a machine fluid 94 (shown in phantom) within the machine 92 enters into a sight glass 96 of the condition monitoring pod assembly 90 and is visible to a person monitoring the condition of the machine fluid 94 through at least a portion of the sight glass 96. The sight glass 96 extends away from the machine 92 and may be visible from multiple different perspectives to enhance the readability of the sight glass 96 as compared to conventional planar sight glasses. In some embodiments, the machine 92 may include a housing 93 with an opening 95 sized, dimensioned, and located to overlap a predetermined preferred level of the machine fluid 94 within the housing 93. The condition monitoring pod assembly 90 may be connected to the housing 93 of the machine 92.

Figure 2:
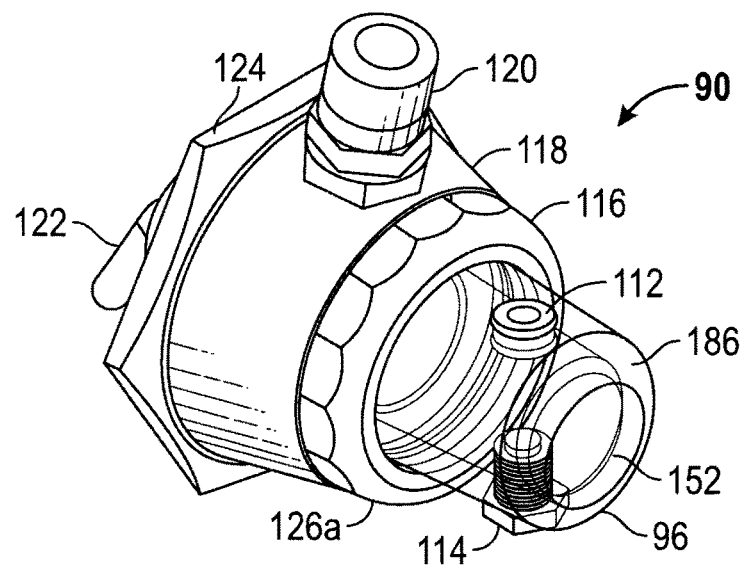
FIG. 2 is a perspective view of an exemplary condition monitoring pod assembly in accordance with the present disclosure.
Figure 3:
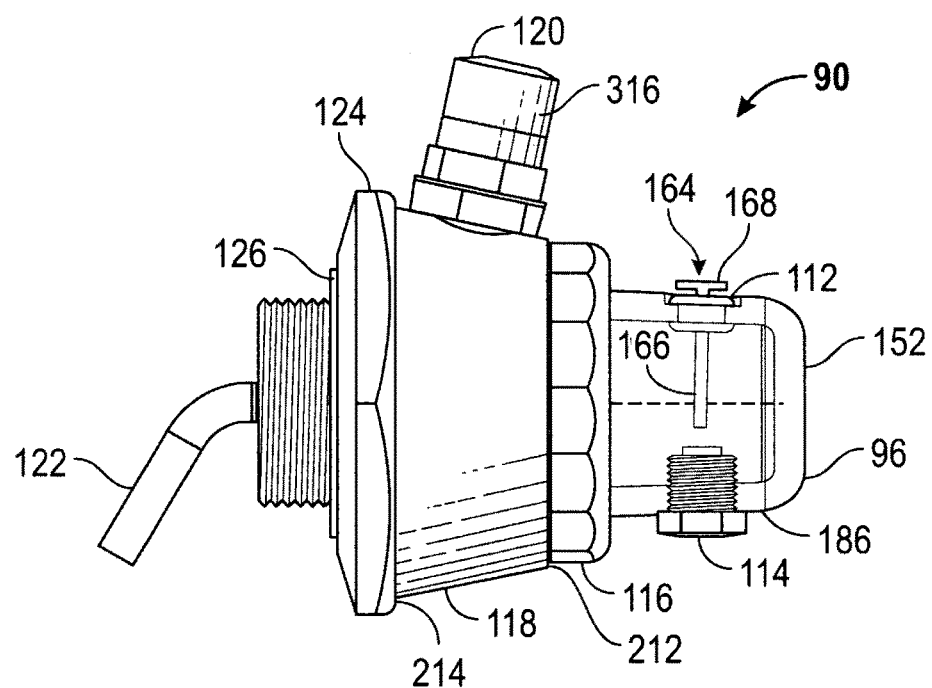
FIG. 3 is a side view of the exemplary condition monitoring pod assembly of FIG. 2
Figure 4:
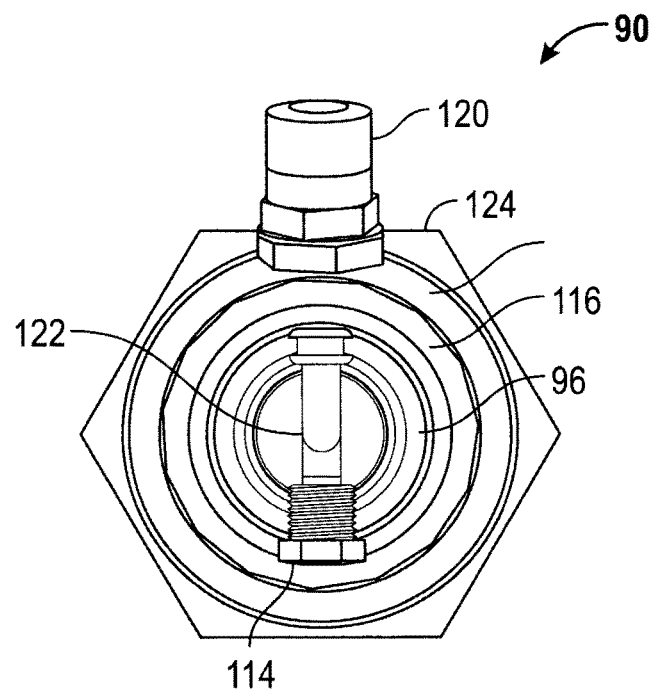
FIG. 4 is a front view of the exemplary condition monitoring pod assembly of FIG. 2.

FIG. 2 is a perspective view of the exemplary condition monitoring pod (CMP) assembly 90 in accordance with the present disclosure. FIG. 3 is a side view of the exemplary condition monitoring pod assembly 90 of FIG. 2. FIG. 4 is a front view of the exemplary condition monitoring pod assembly 90 of FIG. 1. As depicted in the example illustrated in FIGS. 1-4, the condition monitoring pod assembly 90 may comprise the sight glass 96, one or more grommet 112, one or more magnetic plug 114, a coupling 116, a coupling body 118, one or more sample port assembly 120, and one or more pilot tube 122. The condition monitoring pod assembly 90 may further comprise a reducer 124 and one or more shims 126a . . . 126n, only one shim 126 is shown in FIG. 3 for purposes of brevity.

Figure 5:
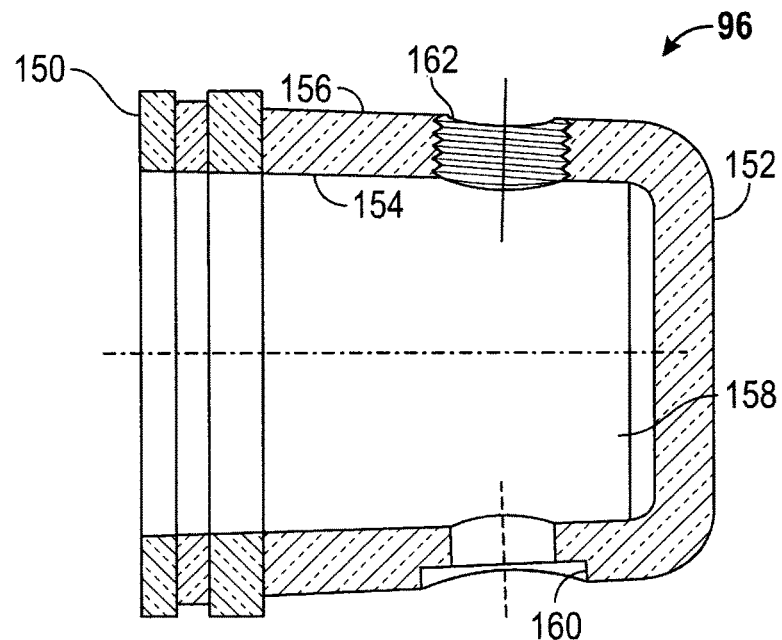
FIG. 5 is a cross-sectional side view of an exemplary sight glass in accordance with the present disclosure.

FIG. 5 is a cross-sectional side view of an exemplary sight glass 96 in accordance with the present disclosure. The sight glass 96 may be at least partially constructed of one or more materials that are transparent to light in a visible region to permit a user to view the machine fluid 94 through the sight glass 96. Non-exclusive examples of such transparent materials include plastic (e.g., acrylic) and glass. The sight glass 96 may be a unitary structure or may be made from multiple separate components that are connected together. When the sight glass 96 is a unitary structure, the sight glass 96 may be formed by a molding process.

The sight glass 96 has an open first end 150, a closed second end 152, an inside surface 154 and an outside surface 156 extending from the open first end 150 to the closed second end 152, which form a cavity 158 within the sight glass 96. The open first end 150 of the sight glass 96 is configured to be attachable to the machine 92 such that the machine fluid 94 is transferable from the machine 92 to the cavity 158 of the sight glass 96 for visible inspection. The second end 152 of the sight glass 96 can be constructed of the one or more materials that are transparent to light in the visible region so that a user may then monitor the machine fluid 94 visually through the inside and outside surfaces 154, 156 and/or the second end 152. This provides a multidimensional view of the machine fluid 94 to aid the user in inspecting the condition of the machine fluid 94. Further, a lower portion of the sight glass 96 may form a bottom of the sight glass 96 thereby supporting any debris that settles thereon for visual inspection.

The sight glass 96 aids the user to visually inspect the condition of the machine fluid 94 so that the user can determine whether the machine fluid 94 is acceptable, or has a problem. Exemplary problems include the machine fluid 94 containing debris, being frothy, and/or having a color indicative of the machine fluid 94 being dirty, being the wrong composition, or being the wrong type of fluid. Additionally, the condition monitoring pod assembly 90 may be positioned such that the user may also determine visually through the sight glass 96 if the machine fluid 94 is at an acceptable or unacceptable volume in the machine, by comparing the level of machine fluid in the sight glass 96 to a predetermined preferred level, which may be indicated by indicia, such as a line, positioned at the predetermined preferred level on the sight glass 96.

The sight glass 96 may have a first port 160 and a second port 162 extending from the cavity 158 through the inside surface 154 and the outside surface 156. One or both of the first and second ports 160 and 162 may be threaded. In the example shown in FIG. 5, the first port 160 is unthreaded and designed to accept the grommet 112; the second port 162 is threaded and designed to accept the magnetic plug 114.

In one embodiment, a probe 164 (FIG. 3) may extend through the grommet 112 within the first port 160 and into the cavity 158 of the sight glass 96 and into the machine fluid 94 therein. The probe 164 may have a rod 166 and a head 168 extending outwardly from the rod 166. The probe 164 may be a unitary structure, or be formed of two or more components that are connected together.

The probe 164 may be configured to test the machine fluid 94. For example, the rod 166 may have at least one oil test sensor to read a property of the machine fluid 94. The oil test sensor may be selected from a group including a conductivity sensor, a moisture sensor, a particle counter sensor, and a dielectric sensor, for example. In one aspect of the present disclosure, the rod 166 of the probe 164 may be constructed of a similar material as that used for machine components of interest. The rod 166 of the probe 164 may then be used as an indicator of how the machine fluid 94 is affecting the machine components. For example, the rod 166 of the probe 164 may be made of bronze and gears in the machine 92 may be made of bronze. Then, if the bronze rod 166 of the probe 164 is adversely affected by the machine fluid 94, this may indicate that the bronze gears are also being adversely affected by the machine fluid 94. In one example, the rod 166 of the probe 164 may be iron or steel which rusts in the presence of water to indicate the presence of water in the machine fluid 94. The rod 166 may act as a heat sink by being cooler than the machine fluid 94, which may assist condensation forming on the rod 166 in the cavity 158 of the sight glass 96.

In one embodiment, the grommet 112 may be positioned in the first port 160 of the sight glass 96. The grommet 112 may have a sealable access pathway 170 through the grommet 112 to the cavity 158 within the sight glass 96, allowing for access to the machine fluid 94 in the sight glass 96. For example, the rod 166 of the probe 164 may extend through the access pathway 170 into the cavity 158 within the sight glass 96. The grommet 112 may be constructed, at least partially, of a flexible material, such as a rubber or plastic compound. In one embodiment, the grommet 112 may be constructed of a flexible material that may expand sufficiently for the rod 166 of the probe 164 to be inserted in the access pathway 170 and that may contract to seal the first port 160 when the rod 166 of the probe 164 is not present.

In one embodiment, the magnetic plug 114 may be positioned in the second port 162 of the sight glass 96. The magnetic plug 114 may be constructed of threaded metal and may extend into the cavity 158 of the sight glass 96 such that the magnetic plug 114 comes in contact with the machine fluid 94. The magnetic plug 114 may have a magnet that attracts and retains metal debris in the machine fluid 94. The magnetic plug 114 may be removed from the sight glass 96 and the captured metal debris removed from the magnetic plug 114 and then analyzed to determine certain operating characteristics of the machine 92. For example, the shape or material of the metal debris may indicate what part of the machine 92 the metal debris came from and thus indicate possible problems in that area of the machine 92. The sight glass 96 may be positioned such that the machine fluid 94 is transferred to the sight glass 96 near machine components of interest. In this way, the metal debris captured by the magnetic plug 114 is captured more directly from the area of interest without being damaged by passing through cycles within the machine 92. For instance, bronze debris with a spiral shape may indicate damage to the gears of the machine 92, but if the debris is allowed to pass through the machine 92 the debris' shape may be transformed into a flattened shape, thereby making analysis of origin more difficult.

The sight glass 96 may be rotatably connected to the machine 92 such that the magnetic plug 114 and/or the grommet 112 may be conveniently positioned relative to the machine fluid 94. For example, before the user removes the magnetic plug 114, the user may rotate the sight glass 96 such that the magnetic plug 114 and the second port 162 are above the level of the machine fluid 94 in the cavity 158 of the sight glass 96 to prevent spillage of the machine fluid 94. In the example shown, the magnetic plug 114 and the probe 164 are supported on opposite sides of the sight glass 96 but are not required to be aligned with one another.

Figure 6:
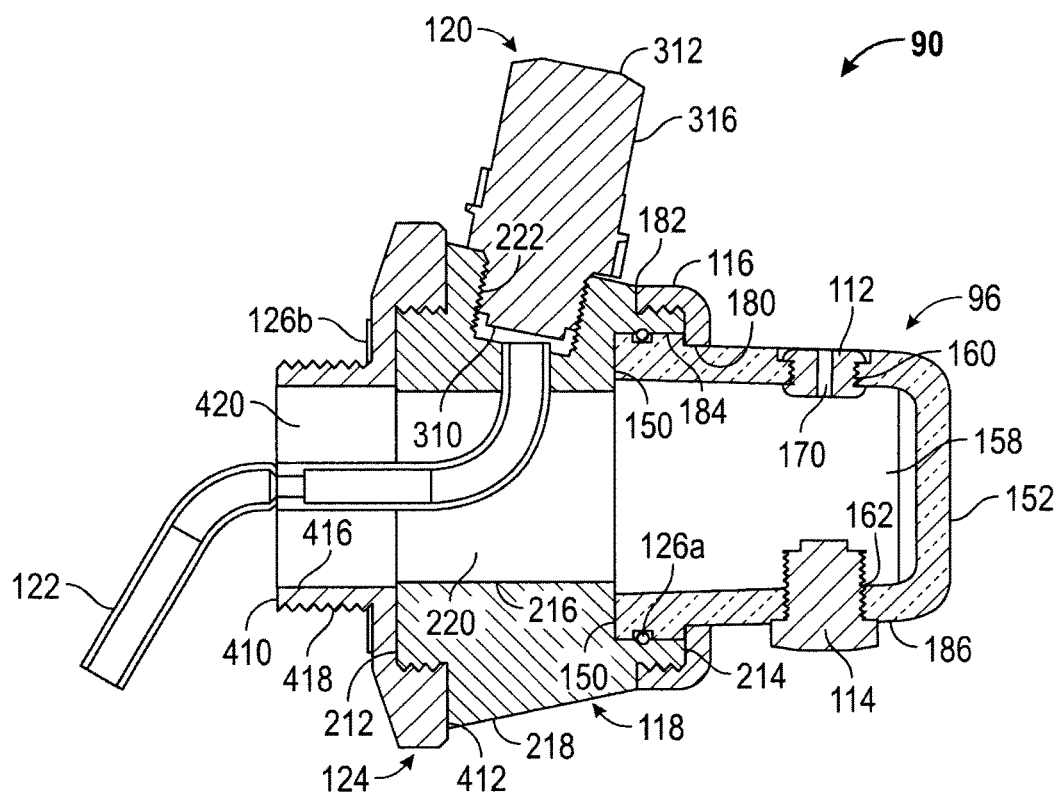
FIG. 6 is a cross-sectional side view of an exemplary condition monitoring pod assembly in accordance with the present disclosure.

Referring now to FIG. 6, FIG. 6 depicts a cross-sectional view of the condition monitoring pod assembly 90 of FIG. 1. In one embodiment, the sight glass 96 is rotatably connected to the machine with the coupling 116 and the coupling body 118. The coupling 116 may have an open first end 180 and an open second end 182. In the example shown, the sight glass 96 has a ridge 184 adjacent to the first end 150 thereof and a window portion 186 extending from the ridge 184 to the second end 152. The first end 180 is sized to pass the window portion 186 and abut against the ridge 184. The coupling 116 may have, but not limited to, a threaded interior surface for mechanically connecting to the coupling body 118. The coupling 116 may permit tightening and loosening adjustments of sight glass 96 for rotation and visual inspection of machine fluid 94, probe 164 and/or magnetic plug 114. The coupling 116 may also permit removability of sight glass 96 for cleaning and replacement. In one embodiment, the coupling 116 is a lock nut.

The coupling body 118 may have an open first end 212 and an open second end 214, an inside surface 216 and an outside surface 218 extending from the open first end 212 to the open second end 214 forming a coupling body cavity 220 such that the machine fluid is transferable from the machine 92 through the coupling body 118 to the sight glass 96. The coupling body 118 may have a port 222 extending from the coupling body cavity 220 through the inside surface 216 and the outside surface 218. The coupling body 118 may be connected to the open first end 150 of the sight glass 96.

For example, as can be seen in FIG. 5, the ridge 184 of the sight glass 96 fits into the second end 214 of the coupling body 118. The coupling 116 may fit over the window portion 186 of the sight glass 96 and be attached to the coupling body 118 such that the sight glass 96 is secured to the coupling body 118 and the sight glass 96 is still rotatable. Further, in at least some embodiments, the coupling body 118 may be connected to the open first end 150 of the sight glass 96 and removable from the sight glass 96 without destruction of the coupling body 118 or the sight glass 96. In one embodiment, one or more seals, such as seal 126a, may be used to seal the connection between the coupling body 118 and the sight glass 96 to prevent machine fluid leaks. The one or more seal 126 may be one or more o-ring or gasket, for example.

In one embodiment, the condition monitoring pod assembly 90 further comprises the sample port assembly 120, also referred to as an oil sampling port assembly 120, connected to the sight glass 96. The sample port assembly 120 may have a first end 310 and a second end 312, an inside surface (not shown) and an outside surface 316 from the first end 310 to the second end 312 forming a sealable access pathway whereby one or more samples of the machine fluid 94 are accessible. The sample port assembly 120 may be positioned directly into the sight glass 96 or may be positioned in the port 222 of the coupling body 118. In one embodiment, the sample port assembly 120 may include a valve to aid the user in drawing the machine fluid 94 out of the machine 92 through the pilot tube 122 and the sample port assembly 120.

The sample port assembly 120 may be utilized to pull a sample of the machine fluid 94 from the machine 92 from a preferred location in the machine 92. For example, the pilot tube 122 may be connected to the first end 310 of the sample port assembly 120 or the inside surface 216 of the coupling body 118. The pilot tube 122 may be a tube of sufficient length and shape to obtain machine fluid 94 from a preferred location in the machine 92 to the sample port assembly 120. The preferred location may be near active flow of the machine fluid 94 so as to access a sample reflective of actual conditions within the machine 92. The sample of machine fluid 94 may be analyzed for composition, cleanliness, moisture content, and so on, to determine if the machine fluid 94 and/or the machine 92 are in a preferred range for efficiency.

In one embodiment, a reducer 124 may be used to adapt the size of the condition monitoring pod assembly 90 to a port (not shown) of the machine 92. The reducer 124 may have an open first end 410, an open second end 412, an inside surface 416 and an outside surface 418 extending from the open first end 410 to the open second end 412 forming a reducer cavity 420 such that the machine fluid 94 is transferable from the machine 92 through the reducer 124 to the sight glass 96. The first end 410 may be a different size than the second end 412 to adapt the condition monitoring pod assembly 90 to be connectable to the port in the machine 92. One or more shims 126, such as shim 126b, may be used to position the sample port 120 relative to machine 92 to provide convenient access for sampling fluid 94. The reducer 124 can be adapted to connect to the port of the machine utilizing any suitable technology, such as a threaded connection.

In an exemplary embodiment, using threaded connections, the condition monitoring pod (CMP) assembly 90 can be installed onto the machine 92 as follows. A volume of the machine fluid 94 is removed so that the machine fluid 94 is located below a port of the machine 92 where the condition monitoring pod assembly 90 will be installed. The port can be created by forming a threaded hole in the machine 92. If the machine 92 already has the port, the port can be opened by removing an original equipment manufacturer sight glass or plug, if any, from the machine 92 so as to provide access to the port. Then, a suitable reducer 124 having an outside diameter matching an inside diameter of the port may be connected to the coupling body 118, and then the reducer 124 may be threaded into the port. One or more shim 126, such as shim 126b, may be used to position sample port 120 relative to machine 92 to provide convenient access to machine fluid 94. Once the condition monitoring pod assembly 90 is installed, an additional volume of the machine fluid 94 can be added to the machine 92.

Once installed, the condition monitoring pod (CMP) assembly 90 can be used to obtain samples of the machine fluid 94 without interrupting operation of the machine 92 by inserting a tube (not shown) through a port of the condition monitoring pod assembly 90 and into the machine fluid 94 of the machine 92. For example, the port can be the second port 162 in the sight glass 96 and in this case, the tube may be disposed through the grommet 112. The tube can be a pipette or a needle of a syringe, for example. Once the tube is positioned in the machine fluid, a sample of the machine fluid 94 is drawn into the tube and the tube is removed from the port. The sample may be applied from the tube to a diagnostic instrument configured to test one or more properties of the machine fluid.

Figure 7:
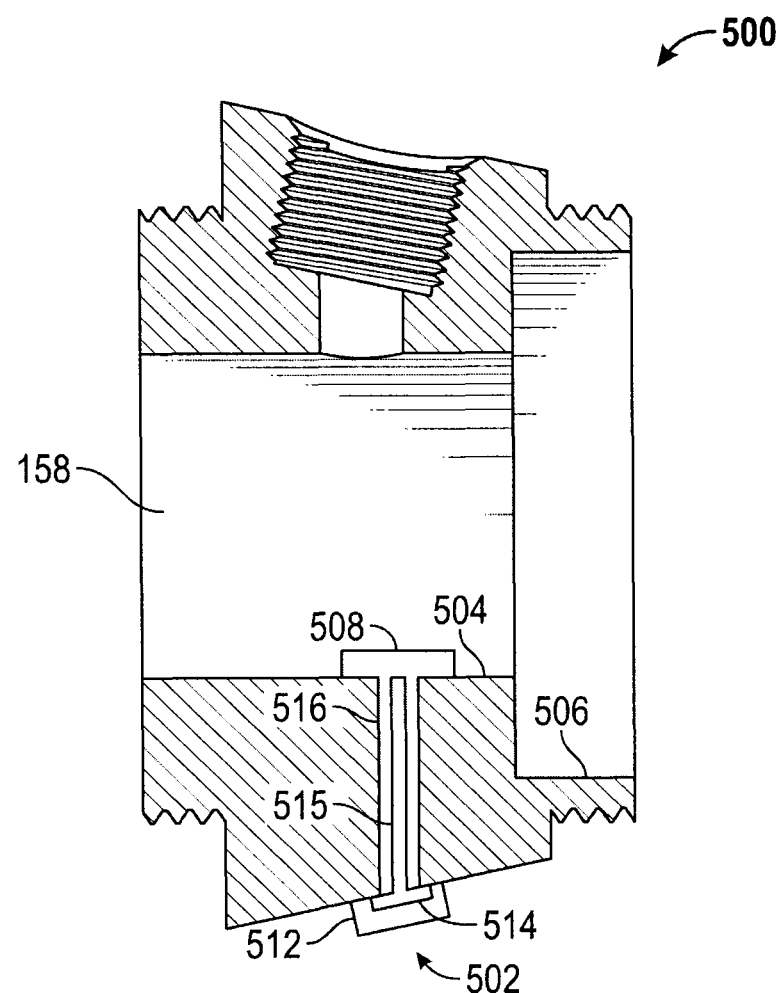
FIG. 7 is a cross-sectional side view of an exemplary coupling body constructed in accordance with the present disclosure and configured to support a lighting system of a version of the condition monitoring pod assembly.

Referring now to FIG. 7, shown therein is another embodiment of a coupling body 500 constructed in accordance with the present disclosure. The coupling body 500 is constructed and used in a similar manner as the coupling body 118 discussed above, with the exception that the coupling body 500 is configured to support a lighting system 502 to illuminate the machine fluid 94 in the sight glass 96 for better inspection of its visual properties (e.g., turbidity, entrained air, foam, varnish, oil level, or the like).

The coupling body 500 may be provided with an inside surface 504, and an open end 506 configured to attach to the first end 150 of the sight glass 96. The lighting system 502 may include a light source 508 connected to the inside surface 504 and positioned to direct light through the open end 506 and into the cavity 158 of the sight glass 96 without the light passing through the outside surface 156 of the sight glass 96 before the light enters the cavity 158. After the light enters the cavity 158, then the light may pass through the inside surface 154 and/or the outside surface 156 of the sight glass 96.

The light source 508 can be a device configured to convert electrical power into photons of light that are preferably within the visible region of the electromagnetic spectrum. For example, the light source 508 may include one or more light emitting diodes or be based upon Xenon-type technologies. The lighting system 502 may also include an actuator 512, such as a button or a switch, configured to connect and disconnect electricity from a power source 514, such as a battery. The actuator 512 can be electrically connected to the light source 508 utilizing any suitable technology, such as wires 515 extending through a bore 516 within the coupling body 500 and between the light source 508 and the actuator 512.

Although the light source 508 is shown as being connected to the coupling body 500, it should be understood that the present disclosure also contemplates the light source 508 being connected to other components of the condition monitoring pod assembly 90, such as the inside surface 154 of the sight glass 96. In this embodiment, the actuator 512 and the power source 514 can also be connected to and supported by the sight glass 96.

Figure 8:
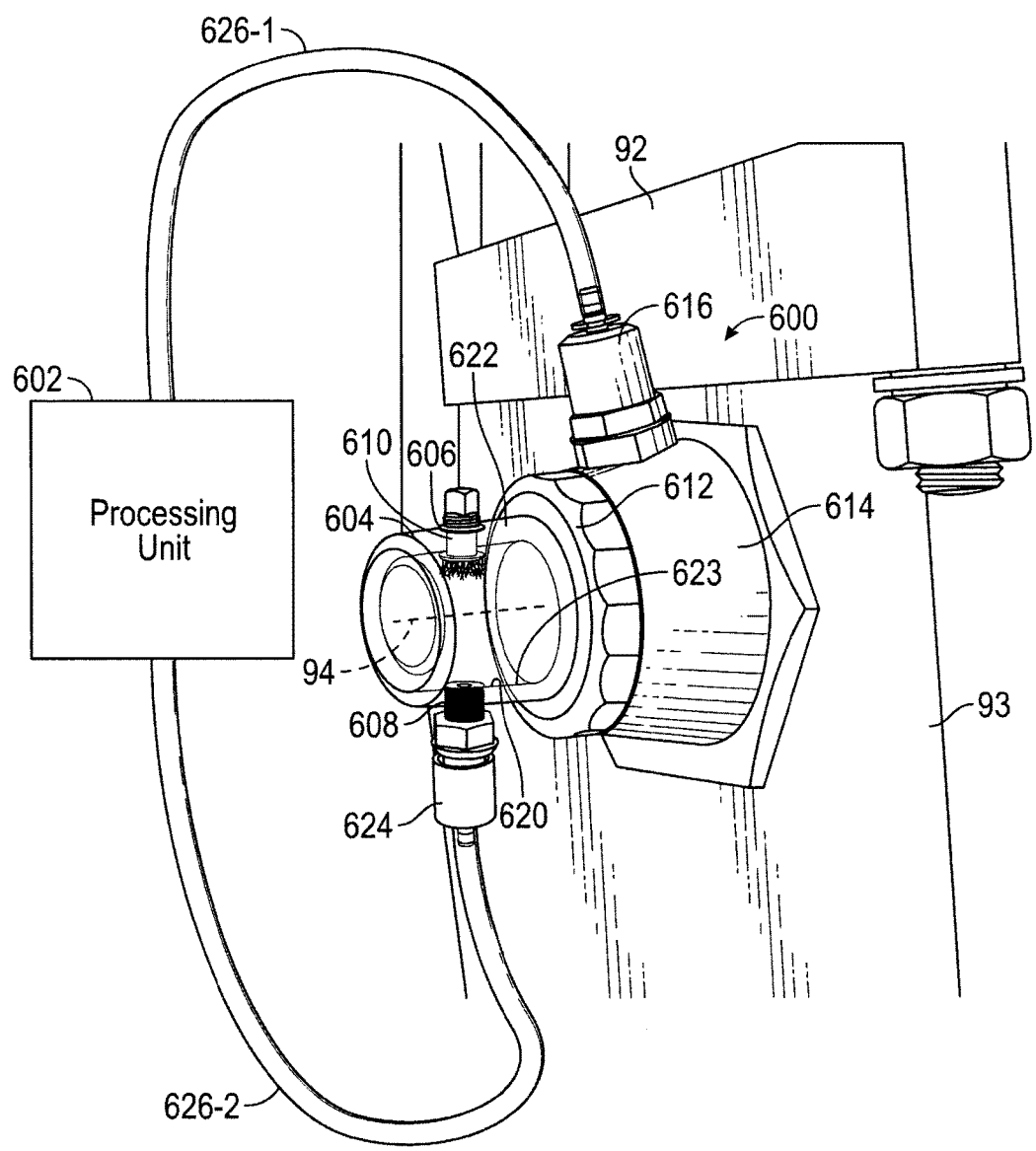
FIG. 8 is a perspective view of an exemplary condition monitoring pod assembly connected to a processing unit and mounted to a machine in accordance with the present disclosure.

Referring now to FIG. 8, shown therein is a condition monitoring pod assembly 600 mounted to the machine 92 and in fluid communication with a processing unit 602. The condition monitoring pod assembly 600 may be implemented similarly to the condition monitoring pod assembly 90. In some embodiments, for example, the condition monitoring pod assembly 600 may be provided with a sight glass 604, a first port 606 extending through the sight glass 604, a second port 608 extending through the sight glass 604, a magnetic plug 610 positioned within the first port 606, a coupling 612, a coupling body 614, an oil sampling port assembly 616 adjacent and connected to the sight glass 604 positioned within a port of the coupling body 614, and one or more pilot tube (not shown). The oil sampling port assembly 616 may be implemented similarly to the oil sampling port assembly 120.

The sight glass 604 may be implemented similarly to the sight glass 96, and may be visible from multiple different perspectives to enhance readability of the machine fluid 94. The sight glass 604 may have an inside surface 620 and an outside surface 622, where the first port 606 and the second port 608 extend between the inside and outside surfaces 620 and 622 of the sight glass 604. The inside surface 620 may define a cavity 623 within the sight glass 604 enabling a portion of the machine fluid 94 to be transferred from the machine 92 into the sight glass 604 indicative of a level of machine fluid 94 within the machine 92. In some embodiments, the first port 606 may be positioned on the sight glass 604 substantially opposite from the second port 608.

The first port 606 may be implemented similar to the second port 162 and be configured to receive the magnetic plug 610. The magnetic plug 610 may be implemented similarly to the magnetic plug 114, as described above. In at least some embodiments, the first port 606 may be positioned on an upper portion of the sight glass 604 such that the magnetic plug 610, extending into the sight glass 604 through the first port 606, may extend into and contact the machine fluid 94 within the sight glass 604. The magnetic plug 610, contacting the machine fluid 94, may have a magnet that attracts and retains metal debris in the machine fluid 94. The magnetic plug 610 may be removed from the sight glass 604 and the captured metal debris removed from the magnetic plug 610 and then analyzed to determine certain operating characteristics of the machine 92, as described above.

The second port 608 may be provided with and receive an oil return port assembly 624. In some embodiments, the oil return port assembly 624 may be implemented similarly to the oil sampling port assembly 120. In some embodiments, the oil return port assembly 624 may be coupled to the processing unit 602 and configured to transfer the machine fluid 94, received from the processing unit 602 and sampled through the first oil sampling port assembly 616 back into the sight glass 604, or the housing 93 of the machine 92, to maintain the level of the machine fluid 94 within the machine 92 and the sight glass 602 and to provide a fluid transfer circulation between the processing unit 602 and the machine 92. The oil return port assembly 624 may or may not include a valve for controlling the flow of the machine fluid 94 therethrough. In some embodiments, one or both of the first and second ports 606 and 608 may be positioned on the coupling body 614, enabling contact with the machine fluid 94 without being positioned within the sight glass 604.

In some embodiments, the coupling body 614 may be implemented similar to the coupling body 118. The coupling body 614 may have a port (not shown) extending through the coupling body 614 to which the oil sampling port assembly 616 may be connected. In some embodiments, the coupling body 614 may be provided with a second port (not shown) extending through the coupling body 614. The second port may be coupled to the processing unit 602, for example by the oil return port assembly 624, and receive the machine fluid 94 from the processing unit 602 to discharge the machine fluid 94 back into the housing 93 of the machine 92.

The oil sampling port assembly 616 may be provided with a first fluid connection 626-1 and the oil return port assembly 624 may be provided with a second fluid connection 626-2. The first fluid connection 626-1 and the second fluid connection 626-2 may place the first oil sampling port assembly 616 and the oil return port assembly 624 in fluid communication with the processing unit 602. The first and second fluid connections 626-1 and 626-2 may be formed from hoses, tubing, piping, or any other suitable hollow tubular member capable of enabling a fluid connection between the processing unit 602 and the first oil sampling port assembly 616 and the oil return port assemblies 624.

In some embodiments, the first fluid connection 626-1 may enable the machine fluid 94 sampled from the machine 92 through the first oil sampling port assembly 616 to be transferred to the processing unit 602. The processing unit 602 may then analyze the machine fluid 94 for one or more property, such as particle count, water and/or viscosity. After being analyzed by the processing unit 602, the machine fluid 94 may be transferred from the processing unit 602 through the second fluid connection 626-2 into the sight glass 604 (on the coupling body 614) via the oil return port assembly 624. In these embodiments, the machine fluid 94 may be sampled without opening the machine 92 and without a cessation of operations of the machine 92. The processing unit 602 can be any type of device that is configured to test, analyze and/or correct the machine fluid 94 to identify and/or correct any deficiencies of the machine fluid 94. For example, the processing unit 602 may test to see if a particle count in the machine fluid 94 exceeds a predetermined level, and if so, the processing unit 602 may circulate the machine fluid 94 through one or more filters to clean the machine fluid 94 prior to transferring the machine fluid 94 into the machine 92 via the condition monitoring pod 600.

The processing unit 602 may be implemented as any suitable diagnostic instrument configured to analyze the machine fluid 94 for one or more property. As described above, the processing unit 602 may retrieve portions of the machine fluid 94 from the machine 92 via the oil sampling port assembly 616, test the machine fluid 94, and return the machine fluid 94 to the machine 92 via the oil return port assembly 624, In some embodiments, the processing unit 602 may additionally or alternatively be in fluid communication with other ports of the condition monitoring pod assembly 600, the sight glass 604, or the coupling body 614. The processing unit 602 may retrieve the machine fluid 94 in a continuous cycle, in at least some embodiments. The machine fluid 94, retrieved by the processing unit 602, may be sampled from an active region of the machine 92 via the pilot tube 122 connected to the oil sampling port assembly 616. As such, the machine fluid 94 may be retrieved from active regions of the machine 92 and returned without compromising the machine fluid 94 or shutting down the machine 92.

CONCLUSION

Conventionally, systems for monitoring and sampling machine lubricants are inefficient, costly, and time consuming. The present disclosure addresses these deficiencies with an apparatus for monitoring and sampling machine fluids 94 with the sight glass 96 or coupling body 118 or 614. The sight glass 96 is at least partially constructed of transparent material and has one or more ports adapted to provide one or more fluid monitoring functions.

The foregoing description provides illustration and description, but is not intended to be exhaustive or to limit the inventive concepts to the precise form disclosed. Modifications and variations are possible in light of the above teachings or may be acquired from practice of the methodologies set forth in the present disclosure.

Even though particular combinations of features are recited in the claims and/or disclosed in the specification, these combinations are not intended to limit the disclosure. In fact, many of these features may be combined in ways not specifically recited in the claims and/or disclosed in the specification. Although each dependent claim listed below may directly depend on only one other claim, the disclosure includes each dependent claim in combination with every other claim in the claim set.

No element, act, or instruction used in the present 26-32 application should be construed as critical or essential to the invention unless explicitly described as such outside of the preferred embodiment. Further, the phrase "based on" is intended to mean "based, at least in part, on" unless explicitly stated otherwise.

What is claimed is:

1. An apparatus for machine fluid monitoring comprising:
   a sight glass at least partially constructed of one or more materials that is transparent to light in a visible region, the sight glass having an open first end, a closed second end, an inside surface and an outside surface extending from the open first end to the closed second end and across the closed second end, the sight glass at least partially surrounding a cavity within the sight glass, the sight glass further having a port extending from the cavity through the inside surface and the outside surface of a portion of the sight glass that is transparent to light in the visible region, the port being separate from the open first end, wherein the open first end of the sight glass is configured to be attachable to a machine such that machine fluid is transferable from the machine to the sight glass, and the closed second end constructed of the one or more materials that are transparent to light in the visible region to allow inspection of machine fluid through the closed second end.

2. The apparatus for machine fluid monitoring of claim 1, further comprising a probe extending through the port and into the cavity of the sight glass.

3. The apparatus for machine fluid monitoring of claim 2, further comprising:
   a grommet positioned in the port of the sight glass, the grommet having a sealable access pathway through the grommet to the cavity within the sight glass, the probe extending through the access pathway into the cavity within the sight glass.

4. The apparatus for machine fluid monitoring of claim 1, wherein the port is a first port, and wherein the sight glass further comprises a second port extending from the cavity through the inside surface and the outside surface.

5. The apparatus for machine fluid monitoring of claim 1, further comprising at least one oil test sensor sized and configured to be positioned in the port.

6. The apparatus for machine fluid monitoring of claim 5, wherein the at least one oil test sensor is from a group consisting of a conductivity sensor, a moisture sensor, a particle counter sensor, and a dielectric sensor.

7. The apparatus for machine fluid monitoring of claim 1, further comprising a magnetic plug sized and configured to be positioned in the port of the sight glass.

8. The apparatus for machine fluid monitoring of claim 1, further comprising a coupling body connected to the first end of the sight glass and removable from the sight glass without destruction of the coupling body or the sight glass, the coupling body configured to be attached to the machine.

9. The apparatus for machine fluid monitoring of claim 8, wherein the coupling body and the first end of the sight glass are connected so as to permit rotation of the sight glass relative to the coupling body while maintaining a fluid tight seal between the sight glass and the coupling body.

10. An apparatus for machine fluid monitoring comprising:
    a transparent sight glass having an open first end, a closed second end, an inside surface and an outside surface extending from the open first end to the closed second end and at least partially surrounding a cavity within the sight glass, and a port extending from the cavity through the inside surface and the outside surface, wherein the open end of the sight glass is configured to be attachable to a machine such that machine fluid is transferable from the machine to the sight glass; and
    a magnetic plug positioned in the port of the sight glass and extending into the cavity within the sight glass such that the magnetic plug is positionable for contact with the machine fluid.

11. The apparatus for machine fluid monitoring of claim 10, further comprising:
    a coupling attached to the first end of the sight glass such that the sight glass is rotatably attachable to the machine via the coupling.

12. An apparatus for machine fluid monitoring comprising:
    a transparent sight glass having an open first end, a closed second end, an inside surface and an outside surface extending from the open first end to the closed second end and at least partially surrounding a cavity within the sight glass, wherein the open first end of the sight glass is configured to be attachable to a machine such that machine fluid is transferable from the machine to the sight glass through an opening sized, dimensioned, and located to overlap a predetermined preferred level of machine fluid within the machine; and
    an oil sampling port assembly adjacent to the sight glass, the oil sampling port assembly having a first end and a second end, an inside surface extending from the first end to the second end forming a sealable access pathway, the oil sampling port assembly including a pilot tube extending adjacent to the first end of the sight glass, the pilot tube extending from the sealable access pathway away from the open first end so as to be extendable into the opening of the machine and into an active flow of the machine fluid inside the machine.

13. The apparatus for machine fluid monitoring of claim 12, further comprising:
    a coupling body connected to the first end of the sight glass, the coupling body having an open first end and an open second end, an inside surface and an outside surface extending from the open first end to the open second end forming a coupling body cavity such that the machine fluid is transferable from the machine through the coupling body to the sight glass, the coupling body further having a port extending from the coupling body cavity through the inside surface and the outside surface; and wherein the oil sampling port assembly is positioned in the port of the coupling body.

14. The apparatus for machine fluid monitoring of claim 12, wherein the oil sampling port assembly includes a valve.

15. An apparatus for machine fluid monitoring comprising:
- a sight glass at least partially constructed of one or more materials that is transparent to light in a visible region, the sight glass having an open first end, a closed second end, an inside surface and an outside surface extending from the open first end to the closed second end and forming a cavity within the sight glass, the sight glass further having a first port and a second port, the first port and the second port extending from the cavity through the inside surface and the outside surface of a portion of the sight glass that is transparent to light in the visible region, wherein the open first end of the sight glass is configured to be attachable to a machine such that machine fluid is transferable from the machine to the sight glass;
- a grommet positioned in the first port of the sight glass, the grommet having a sealable access pathway through the grommet to the cavity within the sight glass,
- a probe extending through the access pathway into the cavity within the sight glass;
- a magnetic plug positioned in the second port of the sight glass and extending into the cavity within the sight glass such that the magnetic plug is positionable for contact with the machine fluid; and
- an oil sampling port assembly adjacent to the sight glass.

16. The apparatus for machine fluid monitoring of claim 15, further comprising:
- a coupling body rotatably connected to the first end of the sight glass, the sight glass rotatable while maintaining a fluid tight seal between the sight glass and the coupling body.

17. An apparatus for machine fluid monitoring, comprising:
- a sight glass at least partially constructed of one or more materials that is transparent to light in a visible region, the sight glass having an open first end, a closed second end, an inside surface and an outside surface extending from the open first end to the closed second end and at least partially surrounding a cavity within the sight glass, the sight glass further having a port extending from the cavity through the inside surface and the outside surface of a portion of the sight glass that is transparent to light in the visible region;
- an oil sampling port assembly adjacent and connected to the sight glass, the oil sampling port assembly having a first end and a second end, an inside surface extending from the first end to the second end forming a sealable access pathway; and
- a magnetic plug positioned in the port of the sight glass and extending into the cavity within the sight glass such that the magnetic plug is positionable for contact with the machine fluid.

\* \* \* \* \*